United States Patent [19]

Galstaun

[11] 4,017,274
[45] Apr. 12, 1977

[54] PROCESS FOR THE METHANATION OF GASES CONTAINING HIGH CONCENTRATION OF CARBON MONOXIDE

[75] Inventor: Lionel S. Galstaun, New York, N.Y.

[73] Assignee: Bechtel Associates Professional Corporation, New York, N.Y.

[22] Filed: Feb. 26, 1976

[21] Appl. No.: 661,565

Related U.S. Application Data

[63] Continuation-in-part of Ser. No. 493,082, July 30, 1974, abandoned, which is a continuation of Ser. No. 272,418, July 17, 1972, abandoned.

[52] U.S. Cl. .......................... 48/214 A; 48/197 R; 260/449 M
[51] Int. Cl.² ................... C10K 3/04; C10G 13/30
[58] Field of Search ......... 48/197 R, 196 R, 214 R; 260/449 M, 449.6; 423/655, 656

[56] References Cited

UNITED STATES PATENTS

| | | | |
|---|---|---|---|
| 3,511,624 | 5/1970 | Humphries et al. | 48/197 R |
| 3,771,261 | 11/1973 | Mandelik et al. | 48/214 |
| 3,954,424 | 5/1976 | Goeke et al. | 48/197 R |

FOREIGN PATENTS OR APPLICATIONS

| | | | |
|---|---|---|---|
| 165,746 | 10/1955 | Australia | 260/449 M |
| 993,974 | 6/1965 | United Kingdom | 48/197 R |

Primary Examiner—Robert L. Lindsay, Jr.
Assistant Examiner—George C. Yeung
Attorney, Agent, or Firm—Pennie & Edmonds

[57] ABSTRACT

This invention relates to a process for the methanation of scrubbed raw gases containing a concentration of carbon monoxide in excess of 3 mole percent and a methane concentration of less than 25 mole percent which comprises reacting a part of the carbon monoxide contained in the raw gases in the presence of an effective amount of at least one steam reforming catalyst contained in a fixed bed, substantially adiabatic reactor with steam, water, or a steam and water mixture provided directly to the reaction zone to effect the shift conversion of a part of the carbon monoxide according to the equation $$CO + H_2O = CO_2 + H_2$$

and simultaneously to effect methanation of the remaining carbon monoxide with hydrogen up to the equilibrium point of the equation $$CO + 3H_2 = CH_4 + H_2O$$

the amount of steam, water, or steam and water mixture being sufficient to maintain the temperature of the reactants below that at which cracking of the methane product in the methanation reaction can take place.

14 Claims, 2 Drawing Figures

PROCESS FOR THE METHANATION OF GASES CONTAINING HIGH CONCENTRATION OF CARBON MONOXIDE

CROSS-REFERENCE TO RELATED APPLICATION

This application is a continuation-in-part of United States application Ser. No. 493,082, filed July 30, 1974, now abandoned, and which in turn is a continuation of U.S. application Ser. No. 272,418, filed July 17, 1972, which is also abandoned.

BACKGROUND OF THE INVENTION

1. Field of the Invention

This invention relates to a process for manufacturing substitute pipeline gas by methanation, the product gas having a calorific value of about 1000 Btu per standard cubic foot, from water gas rich in carbon monoxide and hydrogen. Typical of such water gas is the raw gas generated by known and conventional coal gasification processes.

2. Description of the Prior Art

To convert gas rich in carbon monoxide and hydrogen to substitute pipeline gas, it is generally considered necessary to produce it by the following steps: desulfurization; shift conversion to produce a gas with $H_2/CO$ ratio of about 3:1; $CO_2$ extraction; methanation; and dehydration.

A number of processes have been proposed for the manufacture of substitute pipeline gas from coal. Typical of these processes are the HYGAS Process proposed by the Institute of Gas Technology, the CSC Process of Consolidation Coal Co., the Bi-Gas Process of Bituminous Coal Research, Inc., the Synthane Process of the Bureau of Mines, and the COGAS Process of FMC Corporation. An older process which has been employed commercially for the manufacture of low Btu gas is the Lurgi Process of the Lurgi Gesellschaft of Frankfurt, Germany. All of these processes generate raw gases which are quite rich in carbon monoxide and hydrogen, but are generally free of nitrogen or argon. By combining carbon monoxide and hydrogen via the methanation reaction over a suitable catalyst, the raw gases can be converted to high Btu gas comprising predominantly methane.

The methanation reaction is $$CO + 3H_2 = CH_4 + H_2O$$

It has generally been considered necessary to pre-adjust the $H_2/CO$ ratio to between 3.0:1 and 3.1:1. Since the $H_2/CO$ ratio of the raw gas is substantially below this range, the carbon monoxide in the gas is first reacted with steam over an iron catalyst via the "shift" reaction $$CO + H_2O = CO_2 + H_2$$

This reaction does not normally go to completion. The degree of completeness is limited by equilibrium, which is in turn dependent on the temperature and the concentration of the active species (CO, $H_2O$, $CO_2$, and $H_2$). By an appropriate choice of process conditions it is possible to arrive at a composition wherein the ratio of $H_2$ to CO is in the desired range. Alternatively, a part of the gas can be reacted to a $H_2/CO$ ratio substantially in excess of 3:1, and the reacted gas then mixed with the unreacted remainder to produce the desired 3 to 1 ratio.

At this point, the gas will have a temperature of about 700° F or higher and will generally contain excess $CO_2$ and steam; it may also contain deleterious impurities such as sulfur compounds. The latter must be removed to residuals substantially under 5 ppm and preferably less than 0.2 ppm to protect the nickel catalysts used for methanation which are poisoned by sulfur.

To remove $CO_2$ and sulfur compounds, the gas is cooled to 100°–200° F and treated with alkaline absorbents such as the ethanolamines or the promoted alkali carbonates. If the sulfur compounds are present in quantities higher than about 50–100 ppm, some selective process for extraction of sulfur is preferable so as to make possible the recovery of sulfur in a stream of sufficient concentration to permit conversion to sulfur or sulfuric acid in a practically realizable process. If less than 50 ppm, it is usually more economical to absorb the sulfur on zinc oxide or similar absorbents which can be disposed of by batch removal from the system. A combination of sulfur extraction and final cleanup by absorption on zinc oxide may also be used. This part of the technology is well known and the selection of the specific route is governed mainly by economics.

The gas comprising some pre-formed methane, but now largely hydrogen and carbon monoxide, is ready for methanation. This reaction, $$CO + 3H_2 = CH_4 + H_2O$$

takes place over nickel catalyst and is very highly exothermic. In order for the reaction to start, the gas generally has to be at a temperature of 400° F to 450° F, and therefore, it has to be reheated. Generally, this is done by exchange against the hot effluent from the converter.

Exothermic reaction heat is evolved in such large quantities that if uncontrolled, temperatures would rise to levels which could damage the catalyst and even the reactor vessel. To control the temperature rise, a number of process schemes have been proposed. These schemes generally involve the recycling of methanated product, as well as the staging of the reaction in a series of discrete steps with intercooling between stages.

In one such scheme, raw gas having a $H_2/CO$ ratio equal to about 1.6:1 is cooled, scrubbed, and the particulate matter removed therefrom in step (1), desulfurized in step (2), reheated in step (3), subjected to shift conversion ($CO+H_2O=CO_2+H_2$) in the presence of steam in step (4), cooled and the $CO_2$ removed therefrom in step (5), reheated in step (6), subjected to methanation in step (7) with by-product steam recycled to process, cooled and compressed in step (8) with some product methane being recycled to the methanation reactor to moderate the reaction and dehydrated in step (9).

An example of such a known process is generally described in U.S. Pat. No. 3,511,624, which discloses the catalytic methanation, in at least 2 stages, of mixtures containing carbon monoxide, hydrogen, steam and at least 25% by volume of methane. The mixture is passed in a first stage over a methanation catalyst which is at a temperature of from 200° C to 450° C; steam is then partially removed from the mixture which is then passed into a second stage over a methanation catalyst which is at a temperature within a range lower than the temperature of the mixture leaving the first stage; steam and carbon dioxide are subsequently removed from the mixture. The amount of steam present in each stage is at least sufficient to prevent carbon deposition on the catalyst.

U.S. Pat. No. 3,515,527 discloses a catalyst that can be used in the invention comprising nickel, alumina and an oxide, hydroxide or carbonate of an alkaline earth metal such as barium, the nickel and alumina having been prepared by co-precipitation, the portion being such as to provide from 10% to 30% by weight of the alkaline earth metal and from 25% to 75% by weight of the nickel based on the combined weight of the nickel, alumina and alkaline earth metal. This patent further discloses the production of gases containing methane by reaction of a predominantly hydrocarbon feedstock having a final boiling point of not more than 300° F with steam by passing the feedstock in vapor form and steam at a temperature of from 300° C to 600° C into a bed of the catalyst whereby the bed is maintained at temperatures within the range of 500° C to 600° C.

SUMMARY OF THE INVENTION

Broadly, this invention is a process for the methanation of scrubbed raw gases containing a concentration of carbon monoxide in excess of 3 mole percent and a methane concentration of less than 25 mole percent which comprises reacting a part of the carbon monoxide contained in the raw gases in the presence of an effective amount of at least one steam reforming catalyst contained in a fixed bed, substantially adiabatic reactor with steam, water, or a steam and water mixture provided directly to the reaction zone to effect the shift conversion of a part of the carbon monoxide according to the equation $$CO + H_2O = CO_2 + H_2$$

and simultaneously to effect methanation of the remaining carbon monoxide with hydrogen up to the equilibrium point of the equation $$CO + 3H_2 = CH_4 + H_2O$$

the amount of steam, water, or steam and water mixture being sufficient to maintain the temperature of the reactants below that at which cracking of the methane product in the methanation reaction can take place.

This use of steam or water or a steam and water mixture as the reaction temperature control medium provides a number of substantial advantages as will hereinafter become clear.

The process of this invention in the use of steam, water, or a steam and water mixture permits simultaneous operation of the shift reaction $$CO + H_2O = CO_2 + H_2$$

and eliminates the need of shift conversion as a separate step. This invention thus eliminates the need for steps (4) and (6) as described above.

By providing a suitable chemical driving force, this process reduces or eliminates the possibility of carbon formation according to the Boudouard reaction.

$$2 CO = CO_2 + C$$

which is thermodynamically equivalent to $$H_2 + CO = H_2O + C$$

This can be demonstrated as follows:

| Reaction | | | | Equilibrium Constant |
|---|---|---|---|---|
| 1 | $H_2 + CO$ | = | $H_2O + C$ | $K_1$ |
| 2 | $H_2O + CO$ | = | $H_2 + CO_2$ | $K_2$ |
| 3 | $2 CO$ | = | $CO_2 + C$ | $K_3$ |

The equilibrium constant of reaction 3 (the Boudouard reaction) is simply the product of the constant for reaction 1 ($K_1$) and that of reaction 2 ($K_2$). Reaction 2 is the familiar shift conversion reaction.

Hence, a high steam partial pressure in the reaction system is the thermodynamic equivalent of a high partial pressure of $CO_2$, and both are capable of controlling the laydown of carbon.

The expensive heat exchange equipment for cooling the gas in step (5) and all of step (6) of the above-described process scheme is eliminated.

However, the process of this invention does require a catalyst which is capable of economic operation under conditions of high steam partial pressure. For example, conventional nickel containing methanation catalysts are not expected to meet this requirement, mainly because of the known deleterious effect of high temperature steam on the catalyst support as well as the loss of activity of the nickel itself. Steam reforming catalysts, particularly those containing activators to promote low temperature activity and reduce carbon formation, will meet the requirements.

The invention does not relate to the selection of a particular catalyst. Any suitable catalyst, dependent upon the temperature at which the reaction is carried out, would be useful in the process of this invention.

DESCRIPTION OF THE PREFERRED EMBODIMENTS

The invention is broadly applicable to the methanation of sulfurized or desulfurized, scrubbed raw gases. It is advantageous to employ desulfurized, scrubbed raw gases since known, commercially available steam reforming catalysts are readily poisoned by even trace quantities of sulfur. The present invention is applicable to the methanation of scrubbed raw gases which have not been desulfurized, as long as the catalyst employed is insensitive to sulfur. Examples of steam reforming catalysts advantageously employed in the method of this invention include the co-precipitated nickel-alumina, alkali promoted catalysts, as well as numerous other known and conventional gasification catalysts.

Figure 1:
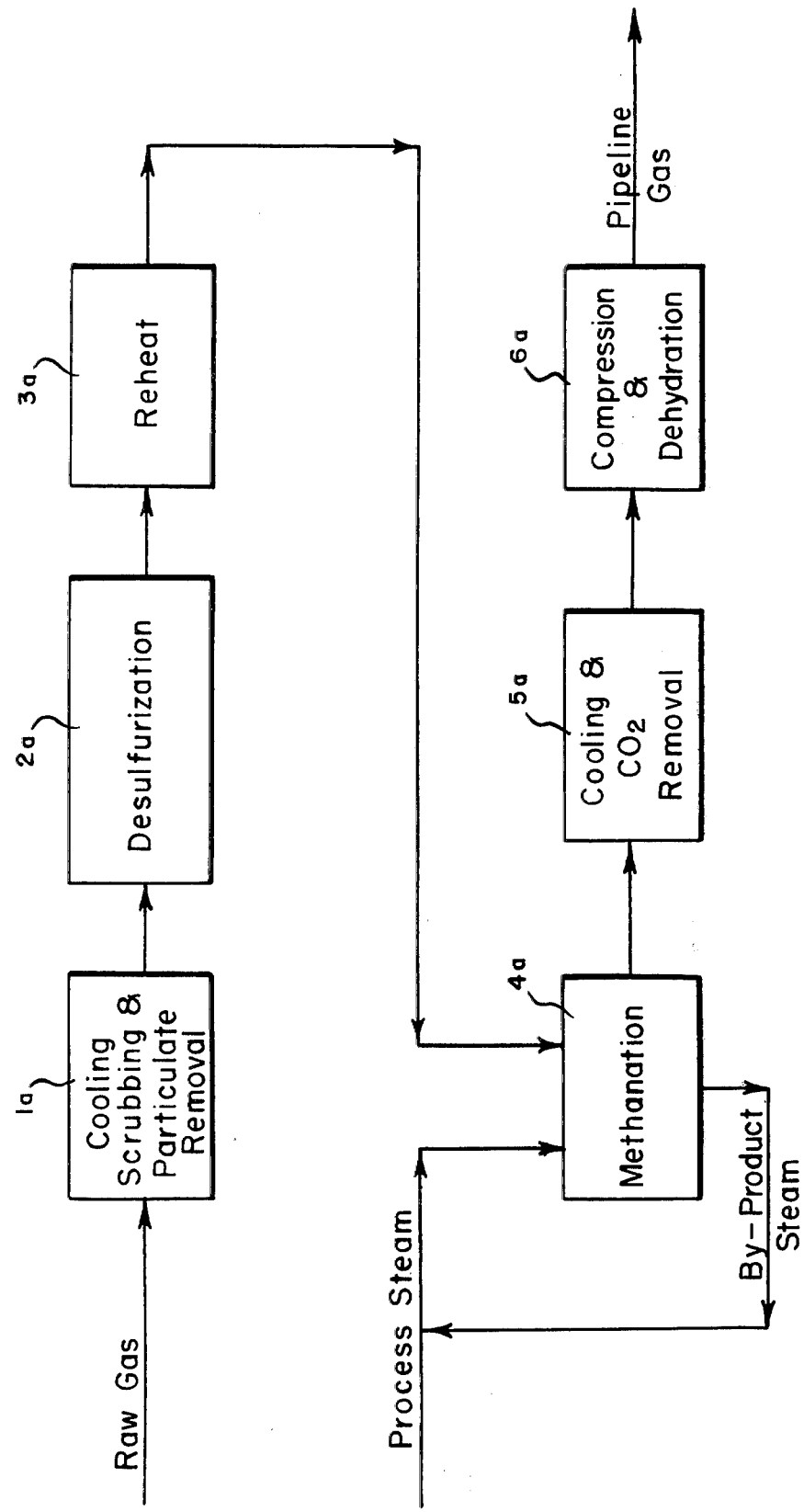
FIG. 1 is a block flow diagram illustrative of the overall process of this invention.

Referring to FIG. 1, raw gas rich in carbon monoxide and hydrogen is cooled, scrubbed and the particulate matter removed therefrom in step 1a, desulfurized in step 2a, reheated in step 3a, subjected to methanation in step 4a with the byproduct steam going to process, cooled and the $CO_2$ content removed therefrom in step 5a and compressed and dehydrated in step 6a.

Figure 2:
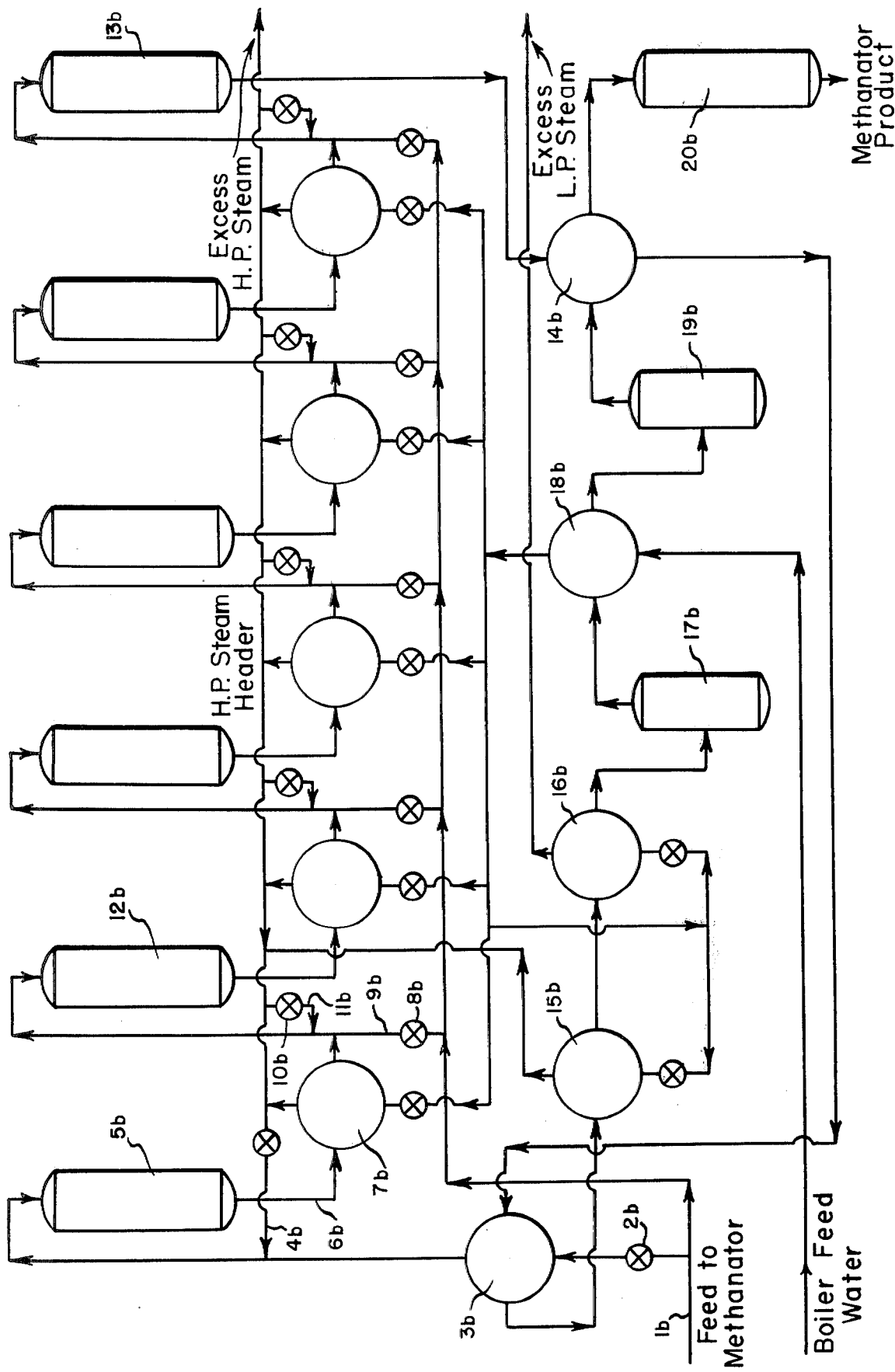
FIG. 2 is a flow diagram of another embodiment of the process of this invention.

Referring to FIG. 2, there are seven stages or methanation reactors. As will be hereinafter made apparent, there can be more or less than this number of stages. Cold feed gas suitable for methanation, pretreated in accordance with the requirements of the catalyst in use, enter via line 1b. A portion of the feed flows through valve 2b to exchanger 3b where it is preheated to a temperature such that after mixing with steam from line 4b, the mixture of feed and steam will have a temperature high enough to initiate reaction in reactor 5b. With most catalysts, this temperature is in the range from about 400° F to 500° F. The mixture of steam and feed reacts to near equilibrium and exits via line 6b. In order to obtain maximum utilization of the reactors, the proportions of feed and steam are chosen to give an exit temperature of about 900° F or lower so as to attain maximum conversion while preventing thermal cracking of the methane formed. Higher temperatures, up to about 1000° F, may be tolerated under special circumstances; however, it is advantageous to maintain the exit temperature at not higher than about 950° F, and generally to control the exit temperature at about 900° F.

This invention is applicable over a broad temperature range and the above temperature range is not an inherent limitation of the invention. It is, however, advantageous to carry out the process within the above temperature range since known, commercially available steam reforming catalysts are most effective within that range. The instant invention is, however, aplicable to methanation processes employing catalysts effective at temperatures lower than about 400° F or temperatures above about 950°–1000° F. In the latter case, application of this process would be particularly beneficial as the temperature might be permitted to rise to a point below that at which cracking of the methane in the product gas would occur.

The gas flows through line 6b and enters heat exchanger 7b where it is cooled by generating steam at a pressure high enough to be deliverable into the process stream. Cooled first stage effluent exiting from heat exchanger 7b is mixed with cold feed gases metered through valve 8b and conveyed by line 9b. The cooling of reactor 5b effluent in heat exchanger 7b is regulated so that the total feed mixture, including some additional steam from valve 10b and line 11b if needed, is at a temperature in the range for initiating reaction in reactor 12b, the second stage.

The flow through the remaining stages is similar: the cooled effluent is mixed with additional feed and possibly additional steam, and the mixture reacted in the next catalytic stage.

After the next to the last stage, reactor 13b, the gas is cooled sufficiently to condense a large fraction of the steam. This cooling is accomplished successively in heat exchanger 14b where it is exchanged against the last stage feed, followed by heat exchanger 3b, where it exchanges against the first stage feed, then in a high pressure steam generator, 15b, and a low pressure steam generator, 16b. Condensate water is separated in 17b and the cooling continued in heat exchanger 18b, the heat therefrom being used to pre-heat the boiler feed water. The condensate is again separated in 19b. The gases are then reheated to a temperature from about 400° F to 500° F and given a final treatment in reactor 20b.

The methanated product from reactor 20b is cooled and the gases are processed to remove $CO_2$, then dehydrated and compressed to final pipeline pressure. The order of these final steps may be altered but it is advantageous to carry out the final compression after $CO_2$ removal in order to reduce the volume of gas requiring compression.

Although the operating pressure has not been specified, it is usually advantageous to operate at moderate pressure. Methanation is enhanced by high pressure; however, the volume of the gases decreases as methanation proceeds. Therefore, pressure is a variable which is subjecct to economic optimization. For most operations, the optimum pressure can be in the range from about 200 to 500 psig unless the feed gas is delivered at a higher pressure, in which case it can be treated at the available pressure.

The proportioning of the gases fed between methanation stages is also subject to optimization. It is advantageous to increase the proportion of fresh feed from stage to stage, with a minimum amount of fresh feed entering the first stage, a maximum amount entering the next-to-last stage, and no fresh feed entering the last stage. This results in all of the moderating steam being injected into the first stage, with the fresh feed to each successive stage being regulated to hold the maximum reaction temperature of the subsequent reactor to about 900° F.

The amount of steam injected into the first stage using this strategy will depend on the total number of stages.

The following table summarizes the results obtained employing a six stage and a nine stage methanation process system according to this invention.

| | COMPARISON OF SIX STAGE (I) AND NINE STAGE (II) METHANATION PROCESS MATERIAL BALANCES IN MOLES/HR | | | |
|---|---|---|---|---|
| | I | | II | |
| | INLET | OUTLET | INLET | OUTLET |
| STAGE NO. | 1 | | 1 | |
| TEMP. ° F | 450 | 900 | 450 | 900 |
| PRESSURE, PSIG | 384 | 379 | 384 | 379 |
| CO | 6395.7 | 93.9 | 3197.8 | 47.0 |
| $CO_2$ | 18.0 | 4034.2 | 9.0 | 2017.1 |
| $H_2$ | 10288.7 | 7488.4 | 5144.3 | 3724.2 |
| $H_2O$ | 58840.1 | 57109.4 | 29420.1 | 28550.7 |
| $CH_4$ | 1160.7 | 3446.2 | 580.3 | 1723.1 |
| INERTS | 0.0 | 0.0 | 0.0 | 0.0 |
| TOTAL | 76703.2 | 72132.1 | 38351.5 | 36066.1 |
| FRACTION OF FRESH FEED | 0.2 | | 0.1 | |
| MODERATING STEAM, MOLES/HR | 58840.1 | | 29420.1 | |
| STAGE NO. | 2 | | 2 | |
| TEMP. ° F | 451.5 | 895.8 | 464.0 | 897.9 |
| PRESSURE, PSIG | 374 | 369 | 374 | 369 |

-continued

COMPARISON OF SIX STAGE (I) AND NINE STAGE (II) METHANATION PROCESS MATERIAL BALANCES IN MOLES/HR

| | I | | II | |
|---|---|---|---|---|
| | INLET | OUTLET | INLET | OUTLET |
| CO | 6489.6 | 174.2 | 2925.0 | 84.9 |
| $CO_2$ | 4052.2 | 6687.4 | 2025.2 | 3169.2 |
| $H_2$ | 17737.1 | 9331.9 | 8354.1 | 4409.7 |
| $H_2O$ | 61652.1 | 62697.0 | 28554.7 | 29106.9 |
| $CH_4$ | 4606.8 | 8287.0 | 2245.4 | 3945.4 |
| INERTS | 0.00 | 0.00 | 0.0 | 0.0 |
| TOTAL | 94537.8 | 87177.51 | 49643.6 | 45749.2 |
| FRACTION OF FRESH FEED | | 0.2 | | 0.09 |
| MODERATING STEAM, MOLES/HR | | 4542.7 | | 0.0 |

| STAGE NO. | 3 | | 3 | |
|---|---|---|---|---|
| TEMP. °F | 463.7 | 899.2 | 465.2 | 895 |
| PRESSURE, PSIG | 364 | 359 | 364 | 359 |
| CO | 7209.4 | 281.8 | 3282.7 | 126.3 |
| $CO_2$ | 6707.2 | 9435.1 | 3178.1 | 4387.4 |
| $H_2$ | 20649.5 | 10778.1 | 9554.0 | 4921.7 |
| $H_2O$ | 62697.0 | 64168.8 | 29106.9 | 29844.8 |
| $CH_4$ | 9563.7 | 13763.5 | 4521.9 | 6469.1 |
| INERTS | 0.0 | 0.0 | 0.0 | 0.0 |
| TOTAL | 106826.8 | 98427.3 | 49642.6 | 45749.3 |
| FRACTION OF FRESH FEED | | 0.22 | | 0.1 |
| MODERATING STEAM, MOLES/HR | | 0 | | 0 |

| STAGE NO. | 4 | | 4 | |
|---|---|---|---|---|
| TEMP. °F | 463.7 | 899.4 | 466.8 | 887.8 |
| PRESSURE, PSIG | 354 | 349 | 354 | 349 |
| CO | 8276.4 | 408.6 | 3643.9 | 166.6 |
| $CO_2$ | 9457.5 | 12481.0 | 4397.3 | 5689.4 |
| $H_2$ | 23639.0 | 12129.5 | 10580.4 | 5317.0 |
| $H_2O$ | 64168.8 | 65989.7 | 29844.8 | 30737.9 |
| $CH_4$ | 15214.3 | 20058.6 | 7107.4 | 9292.6 |
| INERTS | 0.00 | 0.00 | 0.0 | 0.0 |
| TOTAL | 102756.0 | 111067.4 | 55573.8 | 51203.5 |
| FRACTION OF FRESH FEED | | 0.25 | | 0.11 |
| MODERATING STEAM, MOLES/HR | | 0.0 | | 0 |

| STAGE NO. | 5 | | 5 | |
|---|---|---|---|---|
| TEMP. °F | 496.5 | 799.6 | 465.8 | 884.9 |
| PRESSURE, PSIG | 344 | 339 | 344 | 339 |
| CO | 4565.7 | 132.6 | 4163.9 | 220.7 |
| $CO_2$ | 12492.7 | 12898.9 | 5700.6 | 7179.8 |
| $H_2$ | 18817.1 | 7142.4 | 11747.4 | 5834.6 |
| $H_2O$ | 65989.7 | 69610.5 | 30737.9 | 31722.7 |
| $CH_4$ | 20813.1 | 24840.0 | 10018.0 | 12482.0 |
| INERTS | 0.0 | 0.0 | 0.0 | 0.0 |
| TOTAL | 122678.3 | 114624.4 | 62367.8 | 57439.8 |
| FRACTION OF FRESH FEED | | 0.13 | | 0.125 |
| MODERATING STEAM, MOLES/HR | | 0.0 | | 0 |

| STAGE NO. | 6 | | 6 | |
|---|---|---|---|---|
| TEMP. °F | 450 | 602.5 | 464.4 | 887.9 |
| PRESSURE, PSIG | 324 | 319 | 334 | 329 |
| CO | 132.6 | 35.6 | 4857.6 | 299.4 |
| $CO_2$ | 12898.9 | 11269.2 | 7192.8 | 8916.9 |
| $H_2$ | 7142.4 | 332.7 | 13293.9 | 6516.7 |
| $H_2O$ | 124.1 | 3480.5 | 31722.7 | 32832.7 |
| $CH_4$ | 24840.1 | 26566.7 | 13323.5 | 16157.6 |
| INERTS | 0.00 | 0.00 | 0.0 | 0.0 |
| TOTAL | 45137.1 | 41684.7 | 70390.5 | 64722.3 |
| FRACTION OF FRESH FEED | | 0 | | 0.145 |
| MODERATING STEAM, MOLES/HR | | | | 0 |
| CONDENSATE REMOVED, MOLES/HR | | 69,486.4 | | 0 |

| STAGE NO. | | | 7 | |
|---|---|---|---|---|
| TEMP. °F | | | 462.6 | 892.8 |
| PRESSURE, PSIG | | | 324.0 | 319.0 |
| CO | | | 5735.7 | 413.6 |
| $CO_2$ | | | 8932.2 | 10966.2 |
| $H_2$ | | NONE | 15261.1 | 7430.6 |
| $H_2O$ | | | 32832.7 | 34086.9 |
| $CH_4$ | | | 17144.2 | 30432.3 |
| INERTS | | | 0.0 | 0.0 |
| TOTAL | | | 79905.9 | 73329.5 |
| FRACTION OF FRESH FEED | | | | 0.17 |
| MODERATING STEAM, MOLES/HR | | | | 0 |

| STAGE NO. | | | 8 | |
|---|---|---|---|---|
| TEMP. °F | | | 472.6 | 860.9 |
| PRESSURE, PSIG | | | 314.0 | 309.0 |
| CO | | | 5530.1 | 371.1 |
| $CO_2$ | | | 10980.5 | 12683.4 |
| $H_2$ | | NONE | 15661.5 | 6996.3 |
| $H_2O$ | | | 34086.9 | 35840.0 |
| $CH_4$ | | | 21360.9 | 24816.9 |
| INERTS | | | 0.0 | 0.0 |
| TOTAL | | | 87619.9 | 80707.7 |

-continued

COMPARISON OF SIX STAGE (I) AND NINE STAGE (II) METHANATION PROCESS
MATERIAL BALANCES IN MOLES/HR

| | I | | II | |
|---|---|---|---|---|
| | INLET | OUTLET | INLET | OUTLET |
| FRACTION OF FRESH FEED | | | 0.16 | |
| MODERATING STEAM, MOLES/HR | | | 0 | |
| STAGE NO. | | | 9 | |
| TEMP. °F | | | 450 | 619.6 |
| PRESSURE, PSIG | | | 294 | 289 |
| CO | | | 371.1 | 49.2 |
| $CO_2$ | | | 12683.4 | 11271.5 |
| $H_2$ | | | 6996.3 | 382.9 |
| $H_2O$ | | | 135.6 | 3281.3 |
| $CH_4$ | | | 24816.9 | 26550.7 |
| INERTS | | | 0.0 | 0.0 |
| TOTAL | | | 45003.3 | 31535.6 |
| FRACTION OF FRESH FEED | | | 0.0 | |
| MODERATING STEAM, MOLES/HR | | | 0 | |
| CONDENSATE REMOVED, MOLES/HR | | | 35,704.4 | |

It can be seen from these results that the amount of feed gas is the same in both the six stage and nine stage process and essentially the same quantity of methane is produced. Accordingly, the number of stages is not a limiting parameter for the process of this invention.

The amount of moderating steam injected into the first two stages of the six stage system is 63,382.8 moles/hr. compared to 29,420.1 moles/hr in the nine stage system, a ratio of better than 2 to 1 in favor of the increased number of stages. Consequently, the added cost of providing additional stages must be optimized against the savings in steam. This design basis will require a case by case evaluation, since it is dependent on the economics of steam generation and the cost of added stages.

In the early stages, the shift reaction dominates the methanation reaction by about 2 to 1, whereas in the last stages, the dominant reaction is the consumption of hydrogen by methanation of carbon dioxide. This is a desirable feature of the invention since it minimizes the amount of hydrogen left in the product gas and consequently raises its calorific value.

Although steam has been used as the reaction moderator in the process of this invention, it is completely feasible to use water or a mixture of water and steam for the same purpose. In such a case, the water would be used as a quench between methanation steps. When using water instead of steam, the optimum proportioning of gas feed to the methanation stages would be substantially different; the first stages would get more feed. In such a case, steam would be injected in the early stages with water quench in the lattersteps, or in some instances, a mixture of steam and water can be used in the same stage.

I claim:
1. A process for the methanation of scrubbed raw gases containing a concentration of carbon monoxide in excess of 3 mole percent and a methane concentration of less than 25 mole percent which comprises reacting a part of the carbon monoxide contained in the raw gases in the presence of an effective amount of at least one steam reforming catalyst contained in a fixed bed, substantially adiabatic reactor with steam, water, or a steam and water mixture provided directly to the reaction zone to effect the shift conversion of a part of the carbon monoxide according to the equation

$$CO + H_2O = CO_2 + H_2$$

and simultaneously to effect methanation of the remaining carbon monoxide with hydrogen up to the equilibrium point of the equation $$CO + 3H_2 = CH_4 + H_2O$$

the amount of steam, water, or steam and water mixture being sufficient to maintain the temperature of the reactants below that at which cracking of the methane product in the methanation reaction can take place.

2. The process of claim 1 wherein shift conversion and methanation simultaneously take place in successive stages in a plurality of methanation reactors, each of said reactors being fed both with the effluent of the previous step and with unreacted feed gases.

3. The process of claim 2 wherein the methanation reaction takes place between the carbon dioxide and hydrogen in the later of said successive stages.

4. The process of claim 1 wherein the gases resulting from methanation containing residual hydrogen and carbon dioxide are cooled to a level which is sufficient to condense a substantial portion of the steam present therein to water which is removed from the cooled gases and the gases are subjected to a final methanation reaction to substantially convert the residual hydrogen and carbon dioxide to methane and water.

5. The process of claim 1 wherein the raw gases have been previously desulfurized.

6. The process of claim 5 wherein the catalyst is a co-precipitated nickel-alumina, alkali promoted catalyst.

7. The process of claim 1 wherein the temperature of the reaction medium before methanation takes place is from about 400° F to 500° F and the temperature of the medium after methanation takes place is not higher than about 950° F.

8. The process of claim 1 wherein methanation takes place at about 200 to 500 psig.

9. A process for the methanation of scrubbed raw gases containing a concentration of carbon monoxide in excesss of 3 mole percent and a methane concentration of less than 25 mole percent which comprises:
   a. Feeding the raw gases, together with a temperature moderating amount of steam or water into the first of a series of reaction vessels, the gases being reacted in the presence of an effective amount of at least one steam reforming catalyst to partially react some of the carbon monoxide and hydrogen via the methanation reaction to form methane and water and to simultaneously react another portion of the carbon monoxide with water vapor to form carbon dioxide and hydrogen via the shift conversion reaction;

b. Cooling the effluent gases from the first reactor to a level at about but not below, the temperature required for the methanation and shift conversion reactions to take place;

c. Feeding the effluent gas to the second reaction vessel of said series of reaction vessels with a sufficient quantity of steam provided directly to the reaction zone to moderate the subsequent reaction and to provide sufficient available steam to effect the continued shift conversion and simultaneous methanation reactions in the subsequent reactors, the gases being reacted and the effluent cooled in the same manner as in (a) and (b) above; and d. Continuing to react the gases in the manner described in step (c) in as many subsequent reaction vessels as is necessarily to substantially complete the methanation of the carbon monoxide present in the feed gas.

10. The process of claim 9 wherein the hot effluent from each reactor is used to produce the steam required for the reaction by suitable heat integration in the process scheme.

11. The process of claim 9 wherein the hot gases from the last methanation reactor containing residual hydrogen and carbon dioxide are cooled to a level which is sufficient to condense a substantial portion of the steam present therein to water which is removed from the cooled gases and the gases are subjected to a final methanation reaction, to substantially convert the residual hydrogen and carbon dioxide to methane and water.

12. The process of claim 9 wherein unreacted feed gases are added to said effluent gas for feeding to said second of a series of reaction vessels in step (c).

13. The process of claim 9 wherein the methanation reaction takes place between the carbon dioxide and hydrogen in the later of said series of reaction vessels.

14. The process of claim 9 wherein the raw gases have been previously desulfurized.

* * * * *